US008604010B2

(12) United States Patent
Suzuki et al.

(10) Patent No.: US 8,604,010 B2
(45) Date of Patent: Dec. 10, 2013

(54) METHOD FOR PRODUCING HIGH SAPOGENIN CONTENT COMPOSITION

(75) Inventors: Naho Suzuki, Tokyo (JP); Hidehiko Ishimaru, Tokyo (JP)

(73) Assignee: Lion Corporation, Tokyo (JP)

( * ) Notice: Subject to any disclaimer, the term of this patent is extended or adjusted under 35 U.S.C. 154(b) by 0 days.

(21) Appl. No.: 13/043,083

(22) Filed: Mar. 8, 2011

(65) Prior Publication Data

US 2011/0160169 A1 Jun. 30, 2011

Related U.S. Application Data

(63) Continuation of application No. PCT/JP2009/065651, filed on Sep. 8, 2009.

(30) Foreign Application Priority Data

Sep. 9, 2008 (JP) ................................ 2008-231447

(51) Int. Cl.
*A10N 45/00* (2006.01)
*A61K 31/56* (2006.01)

(52) U.S. Cl.
USPC ........................................................ 514/170

(58) Field of Classification Search
USPC ........................................................ 514/170
See application file for complete search history.

(56) References Cited

U.S. PATENT DOCUMENTS

| | | | | |
|---|---|---|---|---|
| 6,355,249 | B2 * | 3/2002 | Muir et al. | 424/776 |
| 7,811,997 | B2 * | 10/2010 | Zhang et al. | 514/26 |
| 2006/0198908 | A1 | 9/2006 | Ko | |
| 2010/0190968 | A1 * | 7/2010 | Kim et al. | 536/18.1 |

FOREIGN PATENT DOCUMENTS

| | | | |
|---|---|---|---|
| JP | 61-104772 | A | 5/1986 |
| JP | 8-099993 | A | 4/1996 |
| JP | 8-291194 | A | 11/1996 |
| JP | 11-042078 | A | 2/1999 |
| JP | 11-501322 | A | 2/1999 |
| JP | 2007-520418 | A | 7/2007 |
| WO | WO 96/40181 | A1 | 12/1996 |
| WO | WO 03103682 | A1 * | 12/2003 |
| WO | WO 2005/030235 | A1 | 4/2005 |

OTHER PUBLICATIONS

Kawai et al. (1989). "Studies on the Structures of Udosaponins A, B, C, E and F from Aralia cordata THUNB". Chem. Pharm. Bull., 37(9): 2318-2321.*

International Search Report (PCT/ISA/210) issued on Dec. 22, 2009, by Japanese Patent Office as the International Searching Authority for International Application No. PCT/JP2009/065651.

Written Opinion (PCT/ISA/237) issued on Dec. 22, 2009, by Japanese Patent Office as the International Searching Authority for International Application No. PCT/JP2009/065651.

Weissenberg, "Isolation of solasodine and other steroidal alkaloids and sapogenins by direct hydrolysis-extraction of *Solanum* plants or glycosides therefrom", Phytochemistry, 2001, pp. 501-508, vol. 58, No. 3.

Chinese Office Action mailed on Dec. 27, 2012, in corresponding Chinese Patent Application No. 200980135938.1.

Chunfang, *Preparation of the Ginsenoside with Low Polar*, 3 Anhui Chemical Engineering 25 (2005).

Yinhai et al., *Research of acid water extraction from Panax Notoginseng Leaves*, 28(12) Chinese Tradition Patent Medicine 1830-1831 (2006).

* cited by examiner

*Primary Examiner* — Robert T Crow
*Assistant Examiner* — Doan Phan
(74) *Attorney, Agent, or Firm* — Buchanan Ingersoll & Rooney PC

(57) ABSTRACT

A method for producing a high sapogenin content composition, including: allowing a strong acid aqueous solution having a concentration of 0.01 mol/L to 4 mol/L to act on a saponin-containing plant, so as to perform hydrolysis treatment; neutralizing a liquid obtained by the hydrolysis treatment; filtering the liquid so as to obtain a residue; and drying the residue.

12 Claims, No Drawings

METHOD FOR PRODUCING HIGH SAPOGENIN CONTENT COMPOSITION

CROSS-REFERENCE TO RELATED APPLICATIONS

This is a continuation application of PCT/JP2009/065651, filed on Sep. 8, 2009.

BACKGROUND OF THE INVENTION

1. Field of the Invention

The present invention relates to a method of processing a saponin-containing plant such as *Panax notoginseng* into a high sapogenin content composition, which contains the sapogenin in a larger amount. Namely, the present invention relates to a method for producing a high sapogenin content composition using a saponin-containing plant as a raw material.

2. Description of the Related Art

Many plants used for herbal medicines are utilized after processed for the purpose of reducing toxicity, improving preserving properties, and enhancing medicinal effect. As to ginsengs, "Ginseng Radix Rubra" obtained by steaming a ginseng with boiling water, and the like are known as processed ginsengs. For example, a method for producing a processed ginseng for enhancing medicinal effect has been reported, and a method of further increasing a content of a saponin which is a pharmacologically-active component of Ginseng Radix Rubra is disclosed in Japanese Patent Application Laid-Open (JP-A) No. 11-501322.

It has been known that a saponin which is glycoside is poorly absorbed inside of body, but a sapogenin, which is obtained by hydrolyzing a saponin so as to separate a saccharide portion of the saponin therefrom, is absorbed well inside of body, and that the sapogenin exhibits a physiological activity such as an anticancer activity stronger than the saponin. A method of processing a ginseng is disclosed, for example, in International Publication No. WO 2005/030235 and this method aims to produce an extract of the ginseng. However, in this method, although the operation is complicated, the amount of a sapogenin is not sufficiently produced, and there are problems that the resultant product is poor in safety and taste for using as a processed ginseng.

Therefore, in the present circumstances, a method of easily producing a high sapogenin content composition, which contains a large amount of a sapogenin and is excellent in taste and safety, using a saponin-containing plant as a raw material, has not been developed yet.

BRIEF SUMMARY OF THE INVENTION

The present invention solves the conventional problems, and aims to achieve the following object. That is, the present invention aims to provide a method for easily producing a high sapogenin content composition, which contains a large amount of a sapogenin and is excellent in taste and safety, using a saponin-containing plant as a raw material.

The inventors of the present invention have been intensively studied to achieve the aforementioned object, and found that a high sapogenin content composition, which contains a large amount of the sapogenin and is excellent in taste and safety, can be produced by an easy method, which includes allowing a strong acid aqueous solution having a certain concentration to act on a saponin-containing plant such as *Panax notoginseng*, so as to perform hydrolysis treatment; neutralizing a liquid obtained by the hydrolysis treatment; filtering the liquid so as to obtain a residue; and drying the residue. Moreover, the inventors of the present invention have been found that by adding lower alcohol such as ethanol during the hydrolysis treatment hydrolysis efficiency is enhanced, and taste and handleability of the resultant high sapogenin content composition are further improved.

The present invention is based on the findings of the inventors of the present invention, and means for solving the problems are as follows:

<1> A method for producing a high sapogenin content composition, including: allowing a strong acid aqueous solution having a concentration of 0.01 mol/L to 4 mol/L to act on a saponin-containing plant, so as to perform hydrolysis treatment; neutralizing a liquid obtained by the hydrolysis treatment; filtering the liquid so as to obtain a residue; and drying the residue.

<2> The method for producing a high sapogenin content composition according to <1>, wherein the hydrolysis treatment is performed in the presence of lower alcohol.

<3> The method for producing a high sapogenin content composition according to <2>, wherein the amount used of the lower alcohol is 1% by volume to 80% by volume relative to the total amount of a hydrolysis solution.

<4> The method for producing a high sapogenin content composition according to any of <2> and <3>, wherein water is added to the liquid obtained by the hydrolysis treatment after the hydrolysis treatment and before the filtering, so as to adjust a concentration of the lower alcohol in the liquid to 50% by volume or less.

<5> The method for producing a high sapogenin content composition according to any of <2> to <4>, wherein the liquid obtained by the hydrolysis treatment is subjected to vacuum concentration after the hydrolysis treatment and before the filtering, so as to adjust a concentration of the lower alcohol in the liquid to 50% by volume or less.

<6> The method for producing a high sapogenin content composition according to any of <1> to <5>, wherein the saponin-containing plant is a plant belonging to a family Araliaceae.

<7> The method for producing a high sapogenin content composition according to <6>, wherein the saponin-containing plant is a plant belonging to any of a genus *Panax* in a family Araliaceae, a genus Eleutherococcus in the family Araliaceae, and a genus *Aralia* in the family Araliaceae.

<8> The method for producing a high sapogenin content composition according to <7>, wherein the plant belonging to the genus *Panax* in the family Araliaceae is any of *Panax notoginseng* and *Panax ginseng.*

<9> The method for producing a high sapogenin content composition according to <7>, wherein the plant belonging to the genus Eleutherococcus in the family Araliaceae is *Acanthopanax senticosus.*

<10> The method for producing a high sapogenin content composition according to <7>, wherein the plant belonging to the genus Aralia in the family Araliaceae is any of *Aralia elata* and *Aralia cordata.*

<11> The method for producing a high sapogenin content composition according to any of <1> to <5>, wherein the saponin-containing plant is a plant belonging to a family Cucurbitaceae.

<12> The method for producing a high sapogenin content composition according to <11>, wherein the saponin-containing plant is a plant belonging to a genus *Gynostemma* in the family Cucurbitaceae.

<13> The method for producing a high sapogenin content composition according to <12>, wherein the plant belonging to the genus *Gynostemma* in the family Cucurbitaceae is *Gynostemma pentaphyllum.*

The present invention can solve the conventional problems and attain the aforementioned object, and can provide a method for easily producing a high sapogenin content composition, which contains a large amount of a sapogenin and is excellent in taste and safety, using a saponin-containing plant as a raw material.

DETAILED DESCRIPTION OF THE INVENTION (Method for Producing a High Sapogenin Content Composition)

A method for producing a high sapogenin content composition of the present invention includes: allowing a strong acid aqueous solution having a certain concentration to act on a saponin-containing plant, so as to perform hydrolysis treatment (hydrolysis treatment step); neutralizing a liquid obtained by the hydrolysis treatment (neutralization step); filtering the liquid so as to obtain a residue (filtering step); and drying the residue (drying step). The method for producing a high sapogenin content composition may further include other steps.

<Saponin-Containing Plant>

In the present invention, the saponin-containing plant used as a raw material is not particularly limited as long as it is a natural product containing a saponin and may be appropriately selected depending on the intended Purpose. Examples of the saponin-containing plant include plants belonging to the genus *Panax* in the family Araliaceae (e.g. *Panax notoginseng* (Burk.) F. H. CHEN, *Panax ginseng* C. A. Meyer, and *Panax japonicum* C. A. Meyer); plants belonging to the genus Eleutherococcus in the family Araliaceae (e.g. *Acanthopanax senticosus* (Rupr. et Maxim.) Harms); plants belonging to the genus Aralia in the family Araliaceae (e.g. *Aralia elata* (Miq.) Seem., and *Aralia cordata* Thumb.); plants belonging to the genus Bupleurum in the family Apiaceae (e.g. *Bupleurum scorzoneraefolium* Willd. var. *Stenophyllum Nakai*); plants belonging to the genus Polygala in the family Polygalaceae (e.g. *Polygala tenuifolia* Willd., and *Polygala senega* L. var. latifolia Torr. et Gray.); plants belonging to the genus *Platycodon* in the family Campanulaceae (e.g. *Platycodon grandiflorum* (Jacq.) A. DC.); plants belonging to the genus *Gynostemma* in the family Cucurbitaceae (e.g. *Gynostemma pentaphyllum* (Thunb. ex Murray) Makino); plants belonging to genus *Glycyrrhiza* in the family Leguminosae (e.g. *Glycyrrhiza glabra* L.); plants belonging to the genus *Achyranthes* in the family Amaranthaceae (e.g. *Achyranthes bidentata* Blume var. tomentosa (Honda) Hara), plants belonging to the genus Lardizabalaceae in the family *Akebia* (e.g. *Akebia trifoliata*); plants belonging to the genus *Ziziphus* in the family Rhamnaceae (e.g. *Zizyphus jujuba* Mill. var. inermis Rehd.); plants belonging to the genus *Anemarrhena* in the family Liliaceae (e.g. *Anemarrhena asphodeloides* Bunge); plants belonging to the genus *Ophiopogon* in the family Liliaceae (e.g. *Ophiopogon japonicus* (L.f.) Ker-Gawl.); and plants belonging to the genus *Dioscorea* in the family Dioscoreaceae (e.g. *Dioscorea tokoro* Makino). Examples of the raw materials include roots of *Panax notoginseng* (Burk.) F. H. CHEN, roots of *Panax ginseng* C. A. Meyer, roots of *Panax japonicum* C. A. Meyer (*Panacis japonici* rhizoma), roots of *Acanthopanax senticosus* (Rupr. et Maxim.) Harms, roots of *Aralia elata* (Miq.) Seem., roots of *Aralia cordata* Thumb., roots of *Bupleurum scorzoneraefolium* Willd. var. *Stenophyllum Nakai* (*Bupleuri radix*), roots of *Polygala tenuifolia* Willd. (*Polygalae radix*), roots of *Polygala senega* L. var. latifolia Torr. et Gray. (*Senegae radix*), roots of *Platycodon grandiflorum* (Jacq.) A. DC., herbs of *Gynostemma pentaphyllum* (Thunb. ex Murray) Makino, roots of *Glycyrrhiza glabra* L., roots of *Achyranthes bidentata* Blume var. tomentosa (Honda) Hara (*Achyranthis Radix*), stems of *Akebia trifoliata* (*Akebiae Caulis*), berries of *Zizyphus jujuba* Mill. var. inermis Rehd. (*Zizyphi Fructus*), rhizomes of *Anemarrhena asphodeloides* Bunge (*Anemarrhenae rhizoma*), roots of *Ophiopogon japonicus* (L. f.) Ker-Gawl. (*Ophiopogonis tuber*), and rhizomes of *Dioscorea tokoro* Makino.

Of these, the roots of *Panax notoginseng* (Burk.) F. H. CHEN, the roots of *Panax ginseng* C. A. Meyer, the roots of *Panax japonicum* C. A. Meyer (*Panacis japonici* rhizoma), the roots of *Acanthopanax senticosus* (Rupr. et Maxim.) Harms, the roots of *Aralia elata* (Miq.) Seem., the roots of *Aralia cordata* Thumb. and the herbs of *Gynostemma pentaphyllum* (Thunb. ex Murray) Makino are preferable, and the roots of *Panax notoginseng* (Burk.) F. H. CHEN are particularly preferable, because the highest yield of sapogenin can be obtained out of those mentioned above.

A saponin-containing plant collected from nature may be used without pretreatment. However, by using the saponin-containing plant which has been subjected to pretreatment, the hydrolysis treatment described below can be more effectively performed. The pretreatment is performed by appropriately combining washing, drying, cutting, crushing, pulverizing, and the like. A saponin-containing plant in a powder form is preferably used. Alternatively, a commercially available saponin-containing plant may be used.

<Hydrolysis Treatment Step>

The hydrolysis treatment step is a step of allowing a strong acid aqueous solution having a certain concentration to act on a saponin-containing plant, so as to hydrolyze a saponin in the plant, to thereby generate a sapogenin which is superior in systemic absorption to the saponin.

The strong acid aqueous solution is not particularly limited as long as an aqueous solution contains strong acid, and may be appropriately selected depending on the intended purpose. Of the strong acid aqueous solutions, an aqueous solution containing inorganic acid, such as hydrochloric acid, phosphoric acid, sulfuric acid, and nitric acid is preferable, and an aqueous solution containing hydrochloric acid is particularly preferable. The concentration of an acid in the strong acid aqueous solution is 0.01 mol/L to 4 mol/L, and preferably 0.5 mol/L to 3 mol/L. When the concentration of the acid is less than 0.01 mol/L, the hydrolysis is insufficiently performed and a sapogenin cannot be efficiently obtained. When the concentration of the acid is more than 4 mol/L, the hydrolysis is excessively performed and there may be disadvantages in cost. By contrast, the concentration of the acid being within the preferable range as described above is advantageous in sufficiently performing hydrolysis so as to obtain a sapogenin with efficiency.

The volume of the strong acid aqueous solution is preferably used 2 times to 20 times the volume of the saponin-containing plant. When the amount used of the strong acid aqueous solution is less than 2 times the volume of the saponin-containing plant, the saponin-containing plant is not sufficiently immersed therein, and the hydrolysis treatment may be insufficiently performed. When the amount used of the strong acid aqueous solution is more than 20 times, there may be disadvantages in cost.

—Use of Lower Alcohol—

The hydrolysis treatment is preferably performed in the presence of lower alcohol. By using the lower alcohol, the affinity between the saponin-containing plant and the strong acid aqueous solution is improved, and the hydrolysis can be efficiently performed. Another advantage of using the lower alcohol is improvement of the taste and handleability of the resultant sapogenin-containing composition. The lower alcohol is not particularly limited and may be appropriately selected depending on the intended purpose. Of these, methanol, ethanol, and propanol are preferable, and ethanol is particularly preferable in terms of safety.

The amount used of the lower alcohol is preferably 1% by volume to 80% by volume, more preferably 10% by volume to 50% by volume, and still more preferably 20% by volume to 40% by volume, relative to the total amount of a hydrolysis solution. When the amount used of the lower alcohol is less than 1% by volume relative to the total amount of the hydrolysis solution, a sapogenin may not be efficiently obtained. When the amount used of the lower alcohol is more than 80% by volume, a sapogenin may not be efficiently obtained, and there may be disadvantages in cost. By contrast, the amount used of the lower alcohol being within the still more preferable range as described above is advantageous in obtaining a sapogenin with efficiency. Note that "total amount of the hydrolysis solution" is the total amount of the reaction solution including the strong acid aqueous solution and the lower alcohol.

The volume of the total amount of the reaction solution (total amount of the hydrolysis solution) including the strong acid aqueous solution and the lower alcohol is preferably 2 times to 20 times the volume of the saponin-containing plant. When the total amount of the reaction solution is less than 2 times the volume of the saponin-containing plant, the saponin-containing plant is not sufficiently immersed therein, and the hydrolysis treatment may not be sufficiently performed. When the total amount of the reaction solution is more than 20 times, there may be disadvantages in cost.

The temperature of the hydrolysis treatment is preferably 60° C. to 100° C., more preferably 70° C. to 90° C. When the temperature is less than 60° C., the hydrolysis treatment may not be sufficiently performed, and a sapogenin may not be efficiently obtained. When the temperature is more than 100° C., special production facilities may be required, causing disadvantages in cost. By contrast, the temperature being within the more preferable range as described above is advantageous in obtaining a sapogenin with efficiency.

The time of the hydrolysis treatment is preferably 30 minutes to 24 hours, more preferably 2 hours to 8 hours. When the time is less than 30 minutes, the hydrolysis may not be sufficiently performed and a sapogenin may not be efficiently obtained. When the time is more than 24 hours, the reaction is excessively proceeded, and there may be disadvantages in cost. By contrast, the treatment time being within the more preferable range as described above is advantageous in obtaining a sapogenin with efficiency.

<Neutralization Step>

The neutralization step is a step of neutralizing a liquid obtained by the hydrolysis treatment after the hydrolysis treatment.

The neutralization is not particularly limited and may be performed by known methods. For example, the neutralization is performed by appropriately adding a strong base aqueous solution such as sodium hydroxide, potassium hydroxide, or the like to the liquid after the hydrolysis treatment. The pH of the neutralized liquid is preferably 5 to 8.

<Filtering Step>

The filtering step is a step of filtering the neutralized liquid after the hydrolysis treatment so as to separate a filtrate and a residue.

The filtering is not particularly limited and may be performed by known methods. After the filtering, washing may be repeated until salt is removed from the residue.

—Water Adding Filtration—

When lower alcohol is not used in the hydrolysis treatment step, the liquid is neutralized, and then filtered straight away. When a lower alcohol is used in the hydrolysis treatment step, for the purpose of promoting the resultant sapogenin remaining in the residue, before the filtering, water is preferably added to the liquid after the hydrolysis treatment so as to decrease the concentration of the lower alcohol. In this case, it is preferred that the amount of the water added be as large as possible, and that the concentration of the lower alcohol in the liquid after the hydrolysis treatment be as low as possible. Specifically, water is added to the liquid, so that the concentration of the lower alcohol becomes preferably 50% by volume or less, more preferably 30% by volume or less, still more preferably 10% by volume or less. When the liquid after the hydrolysis treatment with the concentration of the lower alcohol being more than 50% by volume is filtered, the resultant sapogenin is dissolved into the lower alcohol and discharged as a filtrate. Thus, the sapogenin content in the residue decreases. By contrast, when the concentration of the lower alcohol in the liquid after the hydrolysis treatment is within the still more preferable range as described above, it is advantageous because the sapogenin content in the residue increases.

The saponin is water soluble, but the sapogenin obtained by the hydrolysis treatment is water insoluble.

—Filtration After Vacuum Concentration—

For the purpose of promoting the resultant sapogenin remaining in the residue, before the filtering, the lower alcohol is distilled away by vacuum concentration, so as to decrease the concentration of the lower alcohol in the liquid after the hydrolysis treatment. In this case, the temperature for the vacuum concentration is preferably 70° C. or lower, more preferably 40° C. to 50° C. The lower alcohol is preferably distilled away so as to have a concentration of 50% by volume or less, more preferably 30% by volume or less, still more preferably 10% by volume or less. When liquid after the hydrolysis treatment with the concentration of the lower alcohol being more than 50% by volume is filtered, the resultant sapogenin is dissolved into the lower alcohol and discharged as a filtrate. Thus, the sapogenin content in the residue decreases. By contrast, when the concentration of the lower alcohol in the liquid after the hydrolysis treatment is within the still more preferable range as described above, it is advantageous because the sapogenin content in the residue increases.

The vacuum concentration and the water adding filtration may be performed as individual steps, or as a sequence of steps. When the vacuum concentration and the water adding filtration are performed as a sequence of steps, water is added to the liquid after the vacuum concentration, so as to perform the water adding filtration.

<Drying Step>

The drying step is a step of drying the resultant residue after the filtering step so as to obtain a high sapogenin content composition.

The drying is not particularly limited and may be performed by known methods. For example, normal drying methods such as freeze-drying, air circulation drying, heat drying, drying under reduced pressure, etc. can be used.

<High Sapogenin Content Composition>

In the present invention, by the easy method as described above, a sapogenin is obtained from a saponin contained in the saponin-containing plant as a raw material, to thereby obtain a plant composition containing a high content of the sapogenin (high sapogenin content composition). The sapogenin content in the resultant sapogenin-containing composition is preferably 3% by mass or more, more preferably 5% by mass or more, and still more preferably 10% by mass or more. The sapogenin content is a value measured by a method described in Examples below.

Since the sapogenin is superior in systemic absorption to the saponin, the resultant high sapogenin content composition is expected to exhibit the physiological activity (effect on improving saccharometabolism) which is stronger than that of the saponin-containing plant as a raw material. Since the sapogenin-containing composition obtained by the above-described method is highly safe, and excellent in taste and handleability, the resultant sapogenin-containing composition without any treatment, or after being appropriately treated can be suitably used as an active ingredient of health foods, etc.

EXAMPLES

Hereinafter, the present invention will be specifically described along with Examples and Comparative Examples. However, these Examples shall not be construed as limiting the scope of the present invention.

Example 1

To 1 kg of a *Panax notoginseng* powder, 0.0083 L of hydrochloric acid (35.0% by mass to 37.0% by mass, manufactured by Wako Pure Chemical Industries, Ltd.) and 9.9917 L of water (hydrochloric acid solution for hydrolysis having the concentration of 0.01 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, followed by suction filtration. The resultant residue was dried by heating under reduced pressure, to thereby obtain 167.4 g of a powder (sapogenin-containing composition). Treatment conditions are shown in Table 2.

Example 2

To 1 kg of a *Panax notoginseng* powder, 1.6 L of hydrochloric acid (35.0% by mass to 37.0% by mass, manufactured by Wako Pure Chemical Industries, Ltd.) and 8.4 L of water (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, followed by suction filtration. The resultant residue was dried by heating under reduced pressure, to thereby obtain 173.1 g of a powder (sapogenin-containing composition). Treatment conditions are shown in Table 2.

Example 3

To 1 kg of a *Panax notoginseng* powder, 3.3 L of hydrochloric acid (35.0% by mass to 37.0% by mass, manufactured by Wako Pure Chemical Industries, Ltd.) and 6.7 L of water (hydrochloric acid solution for hydrolysis having the concentration of 4 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, followed by suction filtration. The resultant residue was dried by heating under reduced pressure, to thereby obtain 152.7 g of a powder (sapogenin-containing composition). Treatment conditions are shown in Table 2.

Example 4

To 1 kg of a *Panax notoginseng* powder, 1.6 L of hydrochloric acid (35.0% by mass to 37.0% by mass, manufactured by Wako Pure Chemical Industries, Ltd.), 8.3 L of water and 0.1 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was freeze-dried, to thereby obtain 150.3 g of a powder (sapogenin-containing composition). Treatment conditions are shown in Table 2.

Example 5

To 1 kg of a *Panax notoginseng* powder, 1.6 L of hydrochloric acid (35.0% by mass to 37.0% by mass, manufactured by Wako Pure Chemical Industries, Ltd.), 5.4 L of water and 3.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was freeze-dried, to thereby obtain 162.9 g of a powder (sapogenin-containing composition). Treatment conditions are shown in Table 2.

Example 6

To 1 kg of a *Panax notoginseng* powder, 1.6 L of hydrochloric acid (35.0% by mass to 37.0% by mass, manufactured by Wako Pure Chemical Industries, Ltd.), 0.4 L of water and 8.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was freeze-dried, to thereby obtain 140.5 g of a powder (sapogenin-containing composition). Treatment conditions are shown in Table 3.

Example 7

To 1 kg of a *Panax notoginseng* powder, 1.6 L of hydrochloric acid (35.0% by mass to 37.0% by mass, manufactured by Wako Pure Chemical Industries, Ltd.) and 8.4 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was freeze-dried, to thereby obtain 125.8 g of a powder (sapogenin-containing composition). Treatment conditions are shown in Table 3.

Example 8

To 1 kg of a *Panax notoginseng* powder, 1.6 L of hydrochloric acid (35.0% by mass to 37.0% by mass, manufactured by Wako Pure Chemical Industries, Ltd.), 8.3 L of water and 0.1 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 190 L of distilled water was further added and stirred, followed by suction filtration. The resultant residue was freeze-dried, to thereby obtain 175.7 g of a powder (sapogenin-containing composition). Treatment conditions are shown in Table 3.

Example 9

To 1 kg of a *Panax notoginseng* powder, 1.6 L of hydrochloric acid (35.0% by mass to 37.0% by mass, manufactured by Wako Pure Chemical Industries, Ltd.), 0.4 L of water and 8.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 6.0 L of distilled water was further added and stirred, followed by suction filtration. The resultant residue was freeze-dried, to thereby obtain 135.4 g of a powder (sapogenin-containing composition). Treatment conditions are shown in Table 3.

Example 10

To 1 kg of a *Panax notoginseng* powder, 1.6 L of hydrochloric acid (35.0% by mass to 37.0% by mass, manufactured by Wako Pure Chemical Industries, Ltd.), 0.4 L of water and 8.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 3.3 L of distilled water was further added and stirred, followed by suction filtration. The resultant residue was freeze-dried, to thereby obtain 129.8 g of a powder (sapogenin-containing composition). Treatment conditions are shown in Table 3.

Example 11

To 1 kg of a *Panax notoginseng* powder, 0.53 L of sulfuric acid (96% by mass, manufactured by Wako Pure Chemical Industries, Ltd.) and 9.47 L of water (sulfuric acid solution for hydrolysis having the concentration of 0.96 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, followed by suction filtration. The resultant residue was dried by circulation of hot air, to thereby obtain 147.5 g of a powder (sapogenin-containing composition). Treatment conditions are shown in Table 4.

Example 12

To 1 kg of a *Panax notoginseng* powder, 0.53 L of sulfuric acid (96% by mass, manufactured by Wako Pure Chemical Industries, Ltd.), 6.47 L of water and 3.0 L of 99.5% by volume ethanol (sulfuric acid solution for hydrolysis having the concentration of 0.96 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was dried by circulation of hot air, to thereby obtain 156.8 g of a powder (sapogenin-containing composition). Treatment conditions are shown in Table 4.

Example 13

To 1 kg of a *Panax ginseng* powder, 1.6 L of hydrochloric acid (35.0% by mass to 37.0% by mass, manufactured by Wako Pure Chemical Industries, Ltd.), 5.4 L of water and 3.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was dried by heating under reduced pressure, to thereby obtain 158.8 g of a powder (sapogenin-containing composition). Treatment conditions are shown in Table 4.

Example 14

To 1 kg of a *Gynostemma pentaphyllum* powder, 1.6 L of hydrochloric acid (35.0% $b_y$ mass to 37.0% by mass, manufactured by Wako Pure Chemical Industries, Ltd.), 5.4 L of water and 3.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was dried by circulation of hot air, to thereby obtain 453.0 g of a powder (sapogenin-containing composition). Treatment conditions are shown in Table 4.

Comparative Example 1

A *Panax notoginseng* powder was not hydrolyzed, and the *Panax notoginseng* powder was directly evaluated. Treatment conditions are shown in Table 5.

Comparative Example 2

To 1 kg of a *Panax notoginseng* powder, 0.0033 L of hydrochloric acid (35.0% by mass to 37.0% by mass, manufactured by Wako Pure Chemical Industries, Ltd.) and 9.9967

L of water (hydrochloric acid solution for hydrolysis having the concentration of 0.004 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, followed by suction filtration. The resultant residue was dried by heating under reduced pressure, to thereby obtain 146.5 g of a powder (sapogenin-containing composition). Treatment conditions are shown in Table 5.

Comparative Example 3

To 1 kg of a *Panax notoginseng* powder, 4.17 L of hydrochloric acid (35.0% by mass to 37.0% by mass; manufactured by Wako Pure Chemical Industries, Ltd.) and 5.83 L of water (hydrochloric acid solution for hydrolysis having the concentration of 5 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, followed by suction filtration. The resultant residue was dried by heating under reduced pressure, to thereby obtain 137.8 g of a powder (sapogenin-containing composition). Treatment conditions are shown in Table 5.

Comparative Example 4

To 1 kg of a *Panax notoginseng* powder, 1.22 kg of citric acid (manufactured by Wako Pure Chemical Industries, Ltd.) and 10.0 L of water (citric acid solution for hydrolysis having the concentration of 0.64 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, followed by suction filtration. The resultant residue was dried by heating under reduced pressure, to thereby obtain 753.8 g of a powder (sapogenin-containing composition). Treatment conditions are shown in Table 5.

Comparative Example 5

An Erlenmeyer flask was loaded with 2 L of water, 80 g of a *Panax notoginseng* powder and 4 g of CELLULASE Y-NC (YAKULT PHARMACEUTICAL IND. CO., LTD.), and was kept warm at 50° C. with gently shaking for 5 days. To the Erlenmeyer flask, 8 mL of 1.66 mol/L hydrochloric acid was added, so that the hydrochloric acid concentration in the solution became 0.0066 mon, and the mixture in the Erlenmeyer flask was subjected to heat treatment at 120° C. for 40 minutes, and freeze-dried, to thereby obtain 85 g of a powder. Treatment conditions are shown in Table 5.

Comparative Example 6

A *Panax ginseng* powder was not hydrolyzed, and the *Panax ginseng* powder was directly evaluated. Treatment conditions are shown in Table 6.

Comparative Example 7

To 1 kg of a *Panax ginseng* powder, 0.0033 L of hydrochloric acid (35.0% by mass to 37.0% by mass, manufactured by Wako Pure Chemical Industries, Ltd.), 6.9967 L of water and 3.0 L of 99.5% by volume ethanol (manufactured by Wako Pure Chemical Industries, Ltd.) (hydrochloric acid solution for hydrolysis having the concentration of 0.004 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was dried by heating under reduced pressure, to thereby obtain 139.8 g of a powder (sapogenin-containing composition). Treatment conditions are shown in Table 6.

Comparative Example 8

To 1 kg of a *Panax ginseng* powder, 1.22 kg of citric acid (manufactured by Wako Pure Chemical Industries, Ltd.), 7.0 L of water and 3.0 L of 99.5% by volume ethanol (manufactured by Wako Pure Chemical Industries, Ltd.) (citric acid solution for hydrolysis having the concentration of 0.64 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was dried by heating under reduced pressure, to thereby obtain 724.1 g of a powder (sapogenin-containing composition). Treatment conditions are shown in Table 6.

Comparative Example 9

A *Gynostemma pentaphyllum* powder was not hydrolyzed, and the *Gynostemma pentaphyllum* powder was directly evaluated. Treatment conditions are shown in Table 6.

Comparative Example 10

To 1 kg of a *Gynostemma pentaphyllum* powder, 0.0033 L of hydrochloric acid (35.0% by mass to 37.0% by mass, manufactured by Wako Pure Chemical Industries, Ltd.), 6.9967 L of water and 3.0 L of 99.5% by volume ethanol (manufactured by Wako Pure Chemical Industries, Ltd.) (hydrochloric acid solution for hydrolysis having the concentration of 0.004 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was dried by circulation of hot air, to thereby obtain 436.8 g of a powder (sapogenin-containing composition). Treatment conditions are shown in Table 6.

Comparative Example 11

To 1 kg of a *Gynostemma pentaphyllum* powder, 1.22 kg of citric acid (manufactured by Wako Pure Chemical Industries, Ltd.), 7.0 L of water and 3.0 L of 99.5% by volume ethanol (manufactured by Wako Pure Chemical Industries, Ltd.) (citric acid solution for hydrolysis having the concentration of 0.64 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was dried by circulation of hot air, to thereby obtain 440.2 g of a powder (sapogenin-containing composition). Treatment conditions are shown in Table 6.

Example 15

To 1 kg of a *Panax notoginseng* powder, 1.6 L of hydrochloric acid (35.0% by mass to 37.0% by mass, manufactured by Wako Pure Chemical Industries, Ltd.), 5.4 L of water and 3.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and the liquid was subjected to vacuum concentration until the liquid amount became 50%, so as to remove ethanol. Thereafter, the resultant liquid was suction filtrated, and the resultant residue was freeze-dried, to thereby obtain 170.3 g of a powder (sapogenin-containing composition). Treatment conditions are shown in Table 7.

Example 16

To 1 kg of a *Panax notoginseng* powder, 1.6 L of hydrochloric acid (35.0% by mass to 37.0% by mass, manufactured by Wako Pure Chemical Industries, Ltd.), 0.4 L of water and 8.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and the liquid was subjected to vacuum concentration until the liquid amount became 30%, so as to remove ethanol. Thereafter, the resultant liquid was suction filtrated, and the resultant residue was freeze-dried, to thereby obtain 152.2 g of a powder (sapogenin-containing composition). Treatment conditions are shown in Table 7.

Example 17

To 1 kg of a *Panax notoginseng* powder, 1.6 L of hydrochloric acid (35.0% by mass to 37.0% by mass, manufactured by Wako Pure Chemical Industries, Ltd.), 5.4 L of water and 3.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and the liquid was subjected to vacuum concentration until the liquid amount became 50%, so as to remove ethanol. Thereafter, 25 L of distilled water was added to the resultant liquid, and stirred, followed by suction filtration. The resultant residue was freeze-dried, to thereby obtain 177.2 g of a powder (sapogenin-containing composition). Treatment conditions are shown in Table 7.

Example 18

To 1 kg of a *Panax notoginseng* powder, 1.6 L of hydrochloric acid (35.0% by mass to 37.0% by mass, manufactured by Wako Pure Chemical Industries, Ltd.), 5.4 L of water and 3.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and the liquid was subjected to vacuum concentration until the liquid amount became 50%, so as to remove ethanol. Thereafter, 45 L of distilled water was added to the resultant liquid, and stirred, followed by suction filtration. The resultant residue was freeze-dried, to thereby obtain 174.2 g of a powder (sapogenin-containing composition). Treatment conditions are shown in Table 7.

Example 19

To 1 kg of a *Panax notoginseng* powder, 1.6 L of hydrochloric acid (35.0% by mass to 37.0% by mass, manufactured by Wako Pure Chemical Industries, Ltd.), 0.4 L of water and 8.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and the liquid was subjected to vacuum concentration until the liquid amount became 30%, so as to remove ethanol. Thereafter, 27 L of distilled water was added to the resultant liquid, and stirred, followed by suction filtration. The resultant residue was freeze-dried, to thereby obtain 160.1 g of a powder (sapogenin-containing composition). Treatment conditions are shown in Table 7.

Example 20

To 1 kg of an *Acanthopanax senticosus* powder, 1.6 L of hydrochloric acid (35.0% by mass to 37.0% by mass, manufactured by Wako Pure Chemical Industries, Ltd.), 5.4 L of water and 3.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was freeze-dried, to thereby obtain 150.5 g of a powder (sapogenin-containing composition). Treatment conditions are shown in Table 8.

Comparative Example 12

An *Acanthopanax senticosus* powder was not hydrolyzed, and the *Acanthopanax senticosus* powder was directly evaluated. Treatment conditions are shown in Table 8.

Comparative Example 13

To 1 kg of an *Acanthopanax senticosus* powder, 0.0033 L of hydrochloric acid (35.0% by mass to 37.0% by mass, manufactured by Wako Pure Chemical Industries, Ltd.), 6.9967 L of water and 3.0 L of 99.5% by volume ethanol (manufactured by Wako Pure Chemical Industries, Ltd.) (hydrochloric acid solution for hydrolysis having the concentration of 0.004 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was dried by heating under reduced pressure, to thereby obtain 158.4 g of a powder (sapogenin-containing composition). Treatment conditions are shown in Table 8.

Comparative Example 14

To 1 kg of an *Acanthopanax senticosus* powder, 1.22 kg of citric acid (manufactured by Wako Pure Chemical Industries, Ltd.), 7.0 L of water and 3.0 L of 99.5% by volume ethanol (manufactured by Wako Pure Chemical Industries, Ltd.) (citric acid solution for hydrolysis having the concentration of 0.64 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was dried by heating under reduced pressure, to thereby obtain 703.1 g of a powder (sapogenin-containing composition). Treatment conditions are shown in Table 8.

Example 21

To 1 kg of an *Aralia elata* powder, 1.6 L of hydrochloric acid (35.0% by mass to 37.0% by mass, manufactured by Wako Pure Chemical Industries, Ltd.), 5.4 L of water and 3.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was freeze-dried, to thereby obtain 350.8 g of a powder (sapogenin-containing composition). Treatment conditions are shown in Table 9.

Comparative Example 15

An *Aralia elata* powder was not hydrolyzed, and the *Aralia elata* powder was directly evaluated. Treatment conditions are shown in Table 9.

Comparative Example 16

To 1 kg of an *Aralia elata* powder, 0.0033 L of hydrochloric acid (35.0% by mass to 37.0% by mass, manufactured by Wako Pure Chemical Industries, Ltd.), 6.9967 L of water and 3.0 L of 99.5% by volume ethanol (manufactured by Wako Pure Chemical Industries, Ltd.) (hydrochloric acid solution for hydrolysis having the concentration of 0.004 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was dried by heating under reduced pressure, to thereby obtain 336.7 g of a powder (sapogenin-containing composition). Treatment conditions are shown in Table 9.

Comparative Example 17

To 1 kg of an *Aralia elata* powder, 1.22 kg of citric acid (manufactured by Wako Pure Chemical Industries, Ltd.), 7.0 L of water and 3.0 L of 99.5% by volume ethanol (manufactured by Wako Pure Chemical Industries, Ltd.) (citric acid solution for hydrolysis having the concentration of 0.64 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was dried by heating under reduced pressure, to thereby obtain 912.3 g of a powder (sapogenin-containing composition). Treatment conditions are shown in Table 9.

Example 22

To 1 kg of an *Aralia cordata* powder, 1.6 L of hydrochloric acid (35.0% by mass to 37.0% by mass, manufactured by Wako Pure Chemical Industries, Ltd.), 5.4 L of water and 3.0 L of 99.5% by volume ethanol (manufactured by Wako Pure Chemical Industries, Ltd.) (hydrochloric acid solution for hydrolysis having the concentration of 1.92 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was freeze-dried, to thereby obtain 240.4 g of a powder (sapogenin-containing composition). Treatment conditions are shown in Table 10.

Comparative Example 18

An *Aralia cordata* powder was not hydrolyzed, and the *Aralia cordata* powder was directly evaluated. Treatment conditions are shown in Table 10.

Comparative Example 19

To 1 kg of an Aralia cordata powder, 0.0033 L of hydrochloric acid (35.0% by mass to 37.0% by mass, manufactured by Wako Pure Chemical Industries, Ltd.), 6.9967 L of water and 3.0 L of 99.5% by volume ethanol (manufactured by Wako Pure Chemical Industries, Ltd.) (hydrochloric acid solution for hydrolysis having the concentration of 0.004 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was dried by heating under reduced pressure, to thereby obtain 252.0 g of a powder (sapogenin-containing composition). Treatment conditions are shown in Table 10.

Comparative Example 20

To 1 kg of an *Aralia cordata* powder, 1.22 kg of citric acid (manufactured by Wako Pure Chemical Industries, Ltd.), 7.0 L of water and 3.0 L of 99.5% by volume ethanol (manufactured by Wako Pure Chemical Industries, Ltd.) (citric acid solution for hydrolysis having the concentration of 0.64 mol/L) were added and heated at 80° C. for 6 hours, so as to perform hydrolysis treatment. Next, to the resultant liquid after the hydrolysis treatment, a 5 M sodium hydroxide solution was added to adjust the pH value of the liquid to pH 7.0, and 90 L of distilled water was further added and stirred, followed by suction filtration. The resultant residue was dried by heating under reduced pressure, to thereby obtain 816.7 g of a powder (sapogenin-containing composition). Treatment conditions are shown in Table 10.

[Evaluation]

The sapogenin content and taste of each powder obtained in Examples 1 to 22 and Comparative Examples 1 to 20 were evaluated as described below. The easiness of production of each powder obtained in Examples 1 to 22 and Comparative Examples 1 to 20 was evaluated as described below. The easiness of each waste liquid treatment (operation of solvent recovery) of Examples 1 to 22 and Comparative Examples 1 to 20 was evaluated as described below. The evaluation results are shown in Tables 2 to 10.

<Measurement of Sapogenin Content>

A 1.5 mL Eppendorf tube was loaded with 10 mg of each sample (each of the powders obtained in Examples 1 to 22 and Comparative Examples 1 to 20), and 0.1 mL of an ethanol solution formed by adding 100 mg of magnolol (manufactured by Wako Pure Chemical Industries, Ltd.) as an internal standard in 100 mL of ethanol, and further loaded with ethanol so that the total volume became 1 mL. The mixture was vortexed for 1 minute, and subjected to sonication (ultrasonic treatment) for 5 minutes, to thereby extract sapogenin. The sapogenin was centrifuged at 10,000 rpm for 15 minutes, and a supernatant was filtered using MILLEX-LG filter (manufactured by Millipore Corporation). The filtrate (10 μL) was analyzed by liquid chromatography, and then peak areas of four types of sapogenins (protopanaxatriol, panaxatriol, protopanaxadiol, and panaxadiol) were measured.

—Liquid Chromatography Conditions—

Apparatus: HPLC system (UV-8020) (manufactured by TOSOH CORPORATION)

Column: TSK-GEL ODS-80Ts (4.6 mm diameter×15 cm) (manufactured by TOSOH CORPORATION)

Column temperature: 40° C.

Eluent: water/acetonitrile gradient elution

Flow rate: 1 mL/min

HPLC elution conditions: as shown in Table 1.

TABLE 1

| Minutes | 0 | 20 | 30 | 50 | 60 | 75 | 80 | 95 |
|---|---|---|---|---|---|---|---|---|
| Acetonitrile concentration (%) | 23 | 23 | 70 | 75 | 100 | 100 | 23 | 23 |

—Generation of Calibration Curve—

Standard solutions A, B and C for generating calibration curves of the four types of sapogenins were prepared by adding four sapogenins (all manufactured by Sigma-Aldrich Corporation) and magnolol as an internal standard in ethanol (100 mL) as follows: the amount of protopanaxatriol was A: 10 mg/100 mL, B: 50 mg/100 mL, C: 100 mg/100 mL; the amount of panaxatriol was A: 100 mg/100 mL, B: 250 mg/100 mL, C: 500 mg/100 mL; the amount of protopanaxadiol was A: 5 mg/100 mL, B: 20 mg/100 mL, C: 200 mg/100 mL, the amount of panaxadiol was A: 100 mg/100 mL, B: 500 mg/100 mL, C: 1,000 mg/100 mL; and the amount of magnolol was A, B, C: 10 mg/100 mL. With respect to 104 of the standard solutions A, B and C, peak areas of the sapogenins and the magnolols were measured under the liquid chromatography conditions, and then each calibration curve was generated from a peak area ratio and a concentration ratio between each of the sapogenins and the magnolol.

—Sapogenin Content—

From the calibration curves, the amounts of the four types of the sapogenins in the samples were read, and the sapogenin content was calculated. Note that the sapogenin contents in Tables 2 to 10 are the total of the four types of the sapogenin contents.

<Evaluation of Taste>

Six panelists tasted each powder, and evaluated based on the following scores and criteria.

[Score]

4 points: Tasted Excellent.

3 points: Tasted slightly bitter but good.

2 points: Tasted bitter to a certain degree.

1 point: Tasted strongly bitter.

[Evaluation Criteria of Taste]

A: An average of the scores of the six panelists was 3.5 points or higher.

B: An average of the scores of the six panelists was 2.5 points or higher and less than 3.5 points.

C: An average of the scores of the six panelists was 1.5 points or higher and less than 2.5 points.

D: An average of the scores of the six panelists was less than 1.5 points.

<Evaluation of Easiness of Waste Liquid Treatment (Operation of Solvent Recovery)>

In consideration of the preparation step of each powder, the easiness of waste liquid treatment (operation of solvent recovery) was evaluated based on the following evaluation criteria.

[Evaluation Criteria of the Easiness of Waste Liquid Treatment (Operation of Solvent Recovery)]

A: The amount of the waste liquid to be treated was 50 L or less, when 1 kg of the raw material was treated.

B: The amount of the waste liquid to be treated was more than 50 L, when 1 kg of the raw material was treated.

<Evaluation of Easiness of Production>

In consideration of the preparation step of each powder, the easiness of production was evaluated based on the following evaluation criteria.

[Evaluation Criteria of the Easiness of Production]

A: Time required for production was shorter than 5 days.

B: Time required for production was 5 days or longer.

—: Preparation was not performed.

TABLE 2

| | | Ex. 1 | Ex. 2 | Ex. 3 | Ex. 4 | Ex. 5 |
|---|---|---|---|---|---|---|
| Hydrolysis treatment | Raw material (saponin-containing plant) | | | *Panax notoginseng* | | |
| | Hydrochloric acid (mol/L) | 0.01 | 1.92 | 4 | 1.92 | 1.92 |
| | Sulfuric acid (mol/L) | — | — | — | — | — |
| | Citric acid (mol/L) | — | — | — | — | — |
| | Amount used of ethanol relative to total amount of hydrolysis solution (% by volume) | — | — | — | 1 | 30 |
| | Treatment temperature | 80° C. | 80° C. | 80° C. | 80° C. | 80° C. |
| | Treatment time | 6 hr | 6 hr | 6 hr | 6 hr | 6 hr |

TABLE 2-continued

| | | Ex. 1 | Ex. 2 | Ex. 3 | Ex. 4 | Ex. 5 |
|---|---|---|---|---|---|---|
| Neutralization/filtration/drying | Neutralization | NaOH | NaOH | NaOH | NaOH | NaOH |
| | Removal of ethanol by distillation by vacuum concentration | — | — | — | — | — |
| | Concentration of ethanol in solution after removal of ethanol by distillation by vacuum concentration (% by volume) | — | — | — | — | — |
| | Amount of water added to solution before filtration relative to amount of solution before addition of water (volume) | — | — | — | 9 times | 9 times |
| | Concentration of ethanol in solution after addition of water (% by volume) | — | — | — | 0.1 | 3.0 |
| | Amount of filtrate (waste liquid) when 1 kg of raw material was treated. | 10 L | 10 L | 10 L | 100 L | 100 L |
| | Drying | Heating under reduced pressure | Heating under reduced pressure | Heating under reduced pressure | Freeze-drying | Freeze-drying |
| | (Enzyme treatment, only in Comp. Ex. 5) | — | — | — | — | — |
| Evaluation | Sapogenin content (% by mass) | 3.6 | 6.5 | 7.1 | 9.3 | 12.4 |
| | Taste | A | A | A | A | A |
| | Easiness of production | A | A | A | A | A |
| | Easiness of waste liquid treatment (operation of solvent recovery) | A | A | A | B | B |

TABLE 3

| | | Ex. 6 | Ex. 7 | Ex. 8 | Ex. 9 | Ex. 10 |
|---|---|---|---|---|---|---|
| Hydrolysis treatment | Raw material (saponin-containing plant) | | | *Panax notoginseng* | | |
| | Hydrochloric acid (mol/L) | 1.92 | 1.92 | 1.92 | 1.92 | 1.92 |
| | Sulfuric acid (mol/L) | — | — | — | — | — |
| | Citric acid (mol/L) | — | — | — | — | — |
| | Amount used of ethanol relative to total amount of hydrolysis solution (% by volume) | 80 | 84 | 1 | 80 | 80 |
| | Treatment temperature | 80° C. | 80° C. | 80° C. | 80° C. | 80° C. |
| | Treatment time | 6 hr | 6 hr | 6 hr | 6 hr | 6 hr |
| Neutralization/filtration/drying | Neutralization | NaOH | NaOH | NaOH | NaOH | NaOH |
| | Removal of ethanol by distillation by vacuum concentration | — | — | — | — | — |
| | Concentration of ethanol in solution after removal of ethanol by distillation by vacuum concentration (% by volume) | — | — | — | — | — |
| | Amount of water added to solution before filtration relative to amount of solution before addition of water (volume) | 9 times | 9 times | 19 times | 0.6 times | 0.33 times |
| | Concentration of ethanol in solution after addition of water (% by volume) | 8.0 | 8.4 | 0.05 | 50.0 | 60.0 |
| | Amount of filtrate (waste liquid) when 1 kg of raw material was treated. | 100 L | 100 L | 200 L | 16 L | 13.3 L |
| | Drying | Freeze-drying | Freeze-drying | Freeze-drying | Freeze-drying | Freeze-drying |
| | (Enzyme treatment, only in Comp. Ex. 5) | — | — | — | — | — |
| Evaluation | Sapogenin content (% by mass) | 8.0 | 7.5 | 9.8 | 4.5 | 3.1 |
| | Taste | A | B | A | A | B |
| | Easiness of production | A | A | A | A | A |
| | Easiness of waste liquid treatment (operation of solvent recovery) | B | B | B | A | A |

TABLE 4

| | | Ex. 11 | Ex. 12 | Ex. 13 | Ex. 14 |
|---|---|---|---|---|---|
| Hydrolysis treatment | Raw material (saponin-containing plant) | *Panax notoginseng* | | *Panax ginseng* | *Gynostemma pentaphyllum* |
| | Hydrochloric acid (mol/L) | — | — | 1.92 | 1.92 |
| | Sulfuric acid (mol/L) | 0.96 | 0.96 | — | — |
| | Citric acid (mol/L) | — | — | — | — |
| | Amount used of ethanol relative to total amount of hydrolysis solution (% by volume) | — | 30 | 30 | 30 |
| | Treatment temperature | 80° C. | 80° C. | 80° C. | 80° C. |
| | Treatment time | 6 hr | 6 hr | 6 hr | 6 hr |
| Neutralization/filtration/drying | Neutralization | NaOH | NaOH | NaOH | NaOH |
| | Removal of ethanol by distillation by vacuum concentration | — | — | — | — |
| | Concentration of ethanol in solution after | — | — | — | — |

TABLE 4-continued

| | | Ex. 11 | Ex. 12 | Ex. 13 | Ex. 14 |
|---|---|---|---|---|---|
| | removal of ethanol by distillation by vacuum concentration (% by volume) | | | | |
| | Amount of water added to solution before filtration relative to amount of solution before addition of water (volume) | — | 9 times | 9 times | 9 times |
| | Concentration of ethanol in solution after addition of water (% by volume) | — | 3.0 | 3.0 | 3.0 |
| | Amount of filtrate (waste liquid) when 1 kg of raw material was treated. | 10 L | 100 L | 100 L | 100 L |
| | Drying | Circulation of hot air | Circulation of hot air | Heating under reduced pressure | Circulation of hot air |
| | (Enzyme treatment, only in Comp. Ex. 5) | — | — | — | — |
| Evaluation | Sapogenin content (% by mass) | 10.0 | 11.6 | 4.8 | 3.9 |
| | Taste | A | A | A | A |
| | Easiness of production | A | A | A | A |
| | Easiness of waste liquid treatment (operation of solvent recovery) | A | B | B | B |

TABLE 5

| | | Comp. Ex. 1 | Comp. Ex. 2 | Comp. Ex. 3 | Comp. Ex. 4 | Comp. Ex. 5 |
|---|---|---|---|---|---|---|
| Hydrolysis treatment | Raw material (saponin-containing plant) | | | *Panax notoginseng* | | |
| | Hydrochloric acid (mol/L) | — | 0.004 | 5 | — | 0.0066 |
| | Sulfuric acid (mol/L) | — | — | — | — | — |
| | Citric acid (mol/L) | — | — | — | 0.64 | — |
| | Amount used of ethanol relative to total amount of hydrolysis solution (% by volume) | — | — | — | — | — |
| | Treatment temperature | — | 80° C. | 80° C. | 80° C. | 120° C. |
| | Treatment time | — | 6 hr | 6 hr | 6 hr | 40 min. |
| Neutralization/filtration/drying | Neutralization | — | NaOH | NaOH | NaOH | — |
| | Removal of ethanol by distillation by vacuum concentration | — | — | — | — | — |
| | Concentration of ethanol in solution after removal of ethanol by distillation by vacuum concentration (% by volume) | — | — | — | — | — |
| | Amount of water added to solution before filtration relative to amount of solution before addition of water (volume) | — | — | — | — | — |
| | Concentration of ethanol in solution after addition of water (% by volume) | — | — | — | — | — |
| | Amount of filtrate (waste liquid) when 1 kg of raw material was treated. | — | 10 L | 10 L | 10 L | 10 L |
| | Drying | — | Heating under reduced pressure | Heating under reduced pressure | Heating under reduced pressure | Freeze-drying |
| | (Enzyme treatment, only in Comp. Ex. 5) | — | — | — | — | 50° C., 5 days |
| Evaluation | Sapogenin content (% by mass) | 0.1 | 0.3 | 5.4 | 0.4 | 1.2 |
| | Taste | D | D | C | B | C |
| | Easiness of production | — | A | A | A | B |
| | Easiness of waste liquid treatment (operation of solvent recovery) | — | A | A | A | A |

TABLE 6

| | | Comp. Ex. 6 | Comp. Ex. 7 | Comp. Ex. 8 | Comp. Ex. 9 | Comp. Ex. 10 | Comp. Ex. 11 |
|---|---|---|---|---|---|---|---|
| Hydrolysis treatment | Raw material (saponin-containing plant) | | *Panax ginseng* | | | *Gynostemma pentaphyllum* | |
| | Hydrochloric acid (mol/L) | — | 0.004 | — | — | 0.004 | — |
| | Sulfuric acid (mol/L) | — | — | — | — | — | — |
| | Citric acid (mol/L) | — | — | 0.64 | — | — | 0.64 |
| | Amount used of ethanol relative to total amount of hydrolysis solution (% by volume) | — | 30 | 30 | — | 30 | 30 |
| | Treatment temperature | — | 80° C. | 80° C. | — | 80° C. | 80° C. |
| | Treatment time | — | 6 hr | 6 hr | — | 6 hr | 6 hr |
| Neutralization/filtration/drying | Neutralization | — | NaOH | NaOH | — | NaOH | NaOH |
| | Removal of ethanol by distillation by vacuum concentration | — | — | — | — | — | — |
| | Concentration of ethanol in solution after removal of ethanol by distillation by vacuum concentration (% by volume) | — | — | — | — | — | — |

TABLE 6-continued

| | | Comp. Ex. 6 | Comp. Ex. 7 | Comp. Ex. 8 | Comp. Ex. 9 | Comp. Ex. 10 | Comp. Ex. 11 |
|---|---|---|---|---|---|---|---|
| | Amount of water added to solution before filtration relative to amount of solution before addition of water (volume) | — | 9 times | 9 times | — | 9 times | 9 times |
| | Concentration of ethanol in solution after addition of water (% by volume) | — | 3.0 | 3.0 | — | 3.0 | 3.0 |
| | Amount of filtrate (waste liquid) when 1 kg of raw material was treated. | — | 100 L | 100 L | — | 100 L | 100 L |
| | Drying | — | Heating under reduced pressure | Heating under reduced pressure | — | Circulation of hot air | Circulation of hot air |
| | (Enzyme treatment, only in Comp. Ex. 5) | — | — | — | — | — | — |
| Evaluation | Sapogenin content (% by mass) | 0.1 | 0.3 | 0.4 | 0.4 | 0.6 | 0.4 |
| | Taste | D | C | C | B | C | B |
| | Easiness of production | — | A | A | — | A | A |
| | Easiness of waste liquid treatment (operation of solvent recovery) | — | B | B | — | B | B |

TABLE 7

| | | Ex. 15 | Ex. 16 | Ex. 17 | Ex. 18 | Ex. 19 |
|---|---|---|---|---|---|---|
| Hydrolysis treatment | Raw material (saponin-containing plant) | *Panax notoginseng* | *Panax notoginseng* | *Panax notoginseng* | *Panax notoginseng* | *Panax notoginseng* |
| | Hydrochloric acid (mol/L) | 1.92 | 1.92 | 1.92 | 1.92 | 1.92 |
| | Sulfuric acid (mol/L) | — | — | — | — | — |
| | Citric acid (mol/L) | — | — | — | — | — |
| | Amount used of ethanol relative to total amount of hydrolysis solution (% by volume) | 30 | 80 | 30 | 30 | 80 |
| | Treatment temperature | 80° C. | 80° C. | 80° C. | 80° C. | 80° C. |
| | Treatment time | 6 hr | 6 hr | 6 hr | 6 hr | 6 hr |
| Neutralization/ filtration/ drying | Neutralization | NaOH | NaOH | NaOH | NaOH | NaOH |
| | Removal of ethanol by distillation by vacuum concentration | Until 50% of liquid amount | Until 30% of liquid amount | Until 50% of liquid amount | Until 50% of liquid amount | Until 30% of liquid amount |
| | Concentration of ethanol in solution after removal of ethanol by distillation by vacuum concentration (% by volume) | 6.0 | 50.0 | 6.0 | 6.0 | 50.0 |
| | Amount of water added to solution before filtration relative to amount of solution before addition of water (volume) | — | — | 5 times | 9 times | 9 times |
| | Concentration of ethanol in solution after addition of water (% by volume) | 6.0 | 50.0 | 1.0 | 0.6 | 5.0 |
| | Amount of filtrate (waste liquid) when 1 kg of raw material was treated. | 5 L | 3 L | 30 L | 50 L | 30 L |
| | Drying | Freeze-drying | Freeze-drying | Freeze-drying | Freeze-drying | Freeze-drying |
| | (Enzyme treatment, only in Comp. Ex. 5) | — | — | — | — | — |
| Evaluation | Sapogenin content (% by mass) | 11.5 | 4.2 | 14.6 | 15.2 | 10.9 |
| | Taste | A | A | A | A | A |
| | Easiness of production | A | A | A | A | A |
| | Easiness of waste liquid treatment (operation of solvent recovery) | A | A | A | A | A |

TABLE 8

| | | Ex. 20 | Comp. Ex. 12 | Comp. Ex. 13 | Comp. Ex. 14 |
|---|---|---|---|---|---|
| Hydrolysis treatment | Raw material (saponin-containing plant) | *Acanthopanax senticosus* | | *Acanthopanax senticosus* | |
| | Hydrochloric acid (mol/L) | 1.92 | — | 0.004 | — |
| | Sulfuric acid (mol/L) | — | — | — | — |
| | Citric acid (mol/L) | — | — | — | 0.64 |
| | Amount used of ethanol relative to total amount of hydrolysis solution (% by volume) | 30 | — | 30 | 30 |
| | Treatment temperature | 80° C. | — | 80° C. | 80° C. |
| | Treatment time | 6 hr | — | 6 hr | 6 hr |
| Neutralization/ filtration/ drying | Neutralization | NaOH | — | NaOH | NaOH |
| | Removal of ethanol by distillation by vacuum concentration | — | — | — | — |
| | Concentration of ethanol in solution after removal of ethanol by distillation by vacuum concentration (% by volume) | — | — | — | — |
| | Amount of water added to solution before filtration relative to amount of solution | 9 times | — | 9 times | 9 times |

TABLE 8-continued

| | | Ex. 20 | Comp. Ex. 12 | Comp. Ex. 13 | Comp. Ex. 14 |
|---|---|---|---|---|---|
| | before addition of water (volume) | | | | |
| | Concentration of ethanol in solution after addition of water (% by volume) | 3.0 | — | 3.0 | 3.0 |
| | Amount of filtrate (waste liquid) when 1 kg of raw material was treated. | 100 L | — | 100 L | 100 L |
| | Drying | Freeze-drying | — | Heating under reduced pressure | Heating under reduced pressure |
| | (Enzyme treatment, only in Comp. Ex. 5) | — | — | — | — |
| Evaluation | Sapogenin content (% by mass) | 2.1 | 0.1 | 0.1 | 0.2 |
| | Taste | A | D | C | C |
| | Easiness of production | A | — | A | A |
| | Easiness of waste liquid treatment (operation of solvent recovery) | B | — | B | B |

TABLE 9

| | | Ex. 21 | Comp. Ex. 15 | Comp. Ex. 16 | Comp. Ex. 17 |
|---|---|---|---|---|---|
| Hydrolysis treatment | Raw material (saponin-containing plant) | *Aralia elata* | | *Aralia elata* | |
| | Hydrochloric acid (mol/L) | 1.92 | — | 0.004 | — |
| | Sulfuric acid (mol/L) | — | — | — | — |
| | Citric acid (mol/L) | — | — | — | 0.64 |
| | Amount used of ethanol relative to total amount of hydrolysis solution (% by volume) | 30 | — | 30 | 30 |
| | Treatment temperature | 80° C. | — | 80° C. | 80° C. |
| | Treatment time | 6 hr | — | 6 hr | 6 hr |
| Neutralization/ filtration/ drying | Neutralization | NaOH | — | NaOH | NaOH |
| | Removal of ethanol by distillation by vacuum concentration | — | — | — | — |
| | Concentration of ethanol in solution after removal of ethanol by distillation by vacuum concentration (% by volume) | — | — | — | — |
| | Amount of water added to solution before filtration relative to amount of solution before addition of water (volume) | 9 times | — | 9 times | 9 times |
| | Concentration of ethanol in solution after addition of water (% by volume) | 3.0 | — | 3.0 | 3.0 |
| | Amount of filtrate (waste liquid) when 1 kg of raw material was treated. | 100 L | — | 100 L | 100 L |
| | Drying | Freeze-drying | — | Heating under reduced pressure | Heating under reduced pressure |
| | (Enzyme treatment, only in Comp. Ex. 5) | — | — | — | — |
| Evaluation | Sapogenin content (% by mass) | 1.2 | 0.1 | 0.1 | 0.1 |
| | Taste | A | B | C | B |
| | Easiness of production | A | — | A | A |
| | Easiness of waste liquid treatment (operation of solvent recovery) | B | — | B | B |

TABLE 10

| | | Ex. 22 | Comp. Ex. 18 | Comp. Ex. 19 | Comp. Ex. 20 |
|---|---|---|---|---|---|
| Hydrolysis treatment | Raw material (saponin-containing plant) | *Aralia cordata* | | *Aralia cordata* | |
| | Hydrochloric acid (mol/L) | 1.92 | — | 0.004 | — |
| | Sulfuric acid (mol/L) | — | — | — | — |
| | Citric acid (mol/L) | — | — | — | 0.64 |
| | Amount used of ethanol relative to total amount of hydrolysis solution (% by volume) | 30 | — | 30 | 30 |
| | Treatment temperature | 80° C. | — | 80° C. | 80° C. |
| | Treatment time | 6 hr | — | 6 hr | 6 hr |
| Neutralization/ filtration/drying | Neutralization | NaOH | — | NaOH | NaOH |
| | Removal of ethanol by distillation by vacuum concentration | — | — | — | — |
| | Concentration of ethanol in solution after removal of ethanol by distillation by vacuum concentration (% by volume) | — | — | — | — |
| | Amount of water added to solution before filtration relative to amount of solution before addition of water (volume) | 9 times | — | 9 times | 9 times |
| | Concentration of ethanol in solution after addition of water (% by volume) | 3.0 | — | 3.0 | 3.0 |
| | Amount of filtrate (waste liquid) when 1 kg of raw material was treated. | 100 L | — | 100 L | 100 L |

TABLE 10-continued

| | | Ex. 22 | Comp. Ex. 18 | Comp. Ex. 19 | Comp. Ex. 20 |
|---|---|---|---|---|---|
| | Drying | Freeze-drying | — | Heating under reduced pressure | Heating under reduced pressure |
| | (Enzyme treatment, only in Comp. Ex. 5) | — | — | — | — |
| Evaluation | Sapogenin content (% by mass) | 0.9 | 0.1 | 0.1 | 0.1 |
| | Taste | A | B | C | B |
| | Easiness of production | A | — | A | A |
| | Easiness of waste liquid treatment (operation of solvent recovery) | B | — | B | B |

The results of Tables 2 to 6 show that a high sapogenin content composition having high sapogenin content (at least 3% by mass or more) and excellent taste could be easily obtained by the production method of the present invention.

Examples 1 to 14

From the results of Table 7, it is understood that in Examples 15 to 19, in which the liquid obtained by the hydrolysis treatment was subjected to vacuum concentration so as to remove ethanol, the amount of waste liquid was small compared to those of other Examples and Comparative Examples in which vacuum concentration was not performed, and that the waste liquid treatment (operation of solvent recovery) could be easily performed.

The results of Tables 8 to 10 show that, even though *Acanthopanax senticosus, Aralia elata*, and *Aralia cordata* were respectively used as the saponin-containing plant, by the production method of the present invention (Examples 20 to 22) a high sapogenin content composition having higher sapogenin content and excellent taste could be easily obtained, compared to the production method without using the production method of the present invention (Comparative Examples 12 to 20).

INDUSTRIAL APPLICABILITY

According to the present invention, a saponin-containing plant such as a *Panax notoginseng*, etc. can be processed to a sapogenin-containing composition containing more sapogenin by an easy method (a sapogenin-containing composition can be produced by using a saponin-containing plant as a raw material.). Since a sapogenin is superior in systemic absorption to a saponin, it is expected that a sapogenin-containing composition exhibits the stronger physiological activity (effect on improving saccharometabolism) than that of the saponin-containing plant as a raw material. Thus, the high sapogenin content composition obtained by the production method of the present invention can be suitably used as an active ingredient of health foods, etc.

What is claimed is:

1. A method for producing a high sapogenin content composition, comprising:

allowing a strong acid aqueous solution having a concentration of 0.01 mol/L to 4 mol/L to act on a saponin-containing plant as a raw material, so as to perform hydrolysis treatment;

neutralizing a liquid obtained by the hydrolysis treatment;

filtering the liquid so as to obtain a residue; and drying the residue wherein said composition has a sapogenin content of at least 3% by mass, and wherein the hydrolysis treatment is performed in the presence of lower alcohol.

2. The method for producing a high sapogenin content composition according to claim 1, wherein the amount used of the lower alcohol is 1% by volume to 80% by volume relative to the total amount of a hydrolysis solution.

3. The method for producing a high sapogenin content composition according to claim 1, wherein water is added to the liquid obtained by the hydrolysis treatment after the hydrolysis treatment and before the filtering, so as to adjust a concentration of the lower alcohol in the liquid to 50% by volume or less.

4. The method for producing a high sapogenin content composition according to claim 1, wherein the liquid obtained by the hydrolysis treatment is subjected to vacuum concentration after the hydrolysis treatment and before the filtering, so as to adjust a concentration of the lower alcohol in the liquid to 50% by volume or less.

5. The method for producing a high sapogenin content composition according to claim 1, wherein the saponin-containing plant is a plant belonging to a family Araliaceae.

6. The method for producing a high sapogenin content composition according to claim 5, wherein the saponin-containing plant is a plant belonging to any of a genus *Panax* in a family Araliaceae, a genus *Eleutherococcus* in the family Araliaceae, and a genus *Aralia* in the family Araliaceae.

7. The method for producing a high sapogenin content composition according to claim 6, wherein the plant belonging to the genus *Panax* in the family Araliaceae is any of *Panax notoginseng* and *Panax ginseng*.

8. The method for producing a high sapogenin content composition according to claim 6, wherein the plant belonging to the genus *Eleutherococcus* in the family Araliaceae is *Acanthopanax senticosus*.

9. The method for producing a high sapogenin content composition according to claim 6, wherein the plant belonging to the genus *Aralia* in the family Araliaceae is any of *Aralia elata* and *Aralia cordata*.

10. The method for producing a high sapogenin content composition according to claim 1, wherein the saponin-containing plant is a plant belonging to a family Cucurbitaceae.

11. The method for producing a high sapogenin content composition according to claim 10, wherein the saponin-containing plant is a plant belonging to a genus *Gynostemma* in the family Cucurbitaceae.

12. The method for producing a high sapogenin content composition according to claim 11, wherein the plant belonging to the genus *Gynostemma* in the family Cucurbitaceae is *Gynostemma pentaphyllum*.

* * * * *